US006224898B1

(12) United States Patent
Balogh et al.

(10) Patent No.: US 6,224,898 B1
(45) Date of Patent: May 1, 2001

(54) ANTIMICROBIAL DENDRIMER NANOCOMPOSITES AND A METHOD OF TREATING WOUNDS

(75) Inventors: Lajos Balogh, Ypsilanti, MI (US); Gary L. Hagnauer, Wayland, MA (US); Donald A. Tomalia, Midland, MI (US); Albert T. McManus, San Antonio, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/533,185

(22) Filed: Mar. 23, 2000

(51) Int. Cl.[7] .................................................. A61L 15/22
(52) U.S. Cl. ......................... 424/445; 424/404; 424/405; 424/406; 424/411; 424/423; 424/443; 424/447; 424/448; 424/449; 424/DIG. 16; 424/618; 424/619; 523/122
(58) Field of Search ..................... 424/405, 404, 424/406, 411, 419, 421, 423–437, 443, 445, 447–449, 486, 46, 47, DIG. 16, 618, 619; 523/122

(56) References Cited

U.S. PATENT DOCUMENTS

| 4,036,808 | * | 7/1977 | Rembaum et al. ................ 260/42.51 |
| 4,472,509 | * | 9/1984 | Gansow et al. ....................... 436/548 |
| 5,219,564 | * | 6/1993 | Zalipsky et al. ................... 424/78.17 |
| 5,366,735 | * | 11/1994 | Henry .................................... 424/426 |

OTHER PUBLICATIONS

Roberts et al—Using Starburst Dendrimers—Bioconjugate Chem. 1990 (2) pp. 305–308.*

* cited by examiner

*Primary Examiner*—Neil S. Levy
(74) *Attorney, Agent, or Firm*—Paul S. Clohan, Jr.; U. John Biffoni

(57) ABSTRACT

An antimicrobial agent which is a composite composition of matter comprising a metal or metal-containing compound distributed on or in a dendritic polymer, and a method of treating wounds comprising applying to the wounds said antimicrobial agent. In a most preferred embodiment, said antimicrobial agent comprises discrete nanosized silver or silver containing compounds distributed on or in dendritic polymers.

10 Claims, 2 Drawing Sheets

US 6,224,898 B1

ANTIMICROBIAL DENDRIMER NANOCOMPOSITES AND A METHOD OF TREATING WOUNDS

GOVERNMENT INTEREST

The invention described herein may be manufactured, used and/or licensed by or for the United States Government.

BACKGROUND OF THE INVENTION

1. Field of the Invention

This invention relates generally to antimicrobial compounds and to topical compositions and wound dressings containing antimicrobial compounds. More particularly, the present invention provides dendritic polymer-metal containing composite materials and methods of using such materials for disinfecting and/or sterilizing wounds. Most particularly, the present invention provides composite compositions of matter in which discrete nanosized inorganic materials, for example, silver, cerium, zinc, etc., are distributed on or in a dendritic polymer, and in which the size and size-distribution of the nanosized inorganic materials are determined and controlled by the dendritic polymer.

2. Description of the Related Art

Silver is an effective antimicrobial agent with low toxicity which is particularly important in the topical antibacterial treatment of burn wounds where transient bacteremia is known to frequently occur in association with burn wound manipulation. Silver sulfonamides, particularly silver sulfadiazine (AgSD) has been a standard treatment for burns for at least the past two decades, either alone or in combination with other antibiotics, cerium compounds, zinc compounds and combinations thereof It has been suggested that the basic function of the almost insoluble AgSD may be to slow the release of silver into the superficial wound environment. Silver chloride was assumed to form at the burn wound and absorption of silver was believed to be negligible. In accordance with this assumption, it has been found that serum and tissue silver levels with 10% silver nitrate used in burns produced no difference from that of 1% silver sulfadiazine cream.

However, sulfonamide-resistant organisms have been reported as a frequent consequence of the clinical use of sulfadiazine silver. It was also shown that the sulfadiazine component is not necessary for in vitro sensitivity and that the use of sulfadiazine silver can, in every case, lead to the selection of organisms that are resistant not only to sulfonamides but to antibiotics of clinical consequence. Despite major advances in burn wound management and other supportive care regimens, infection remains the leading cause of morbidity and mortality in the thermally injured patient, and a search for different treatments and new ideas is continuing. Application of silver-binding membranes has recently been suggested to further reduce the likelihood of silver toxicity to retard the movement of silver ions and minimize silver absorption at a healing wound. See Greenfield, E., McManus, A. T., *Nurs. Clin. North Am.*, 1997, 32(2), 297.

SUMMARY OF THE INVENTION

The general objective of the present invention is to provide improved antimicrobial agents which are, for example, useful for the treatment of burn wounds.

Accordingly, it is an object of the present invention to provide an antimicrobial composite composition of matter comprising inorganic materials distributed on or in a polymeric material.

It is a further object of the present invention to provide a composite antimicrobial composition of matter comprising discrete nanosized inorganic materials such as elemental silver, cerium, and zinc or compounds of the same, distributed on or in dendritic polymers.

It is still a further object of the present invention to provide a composite material in which the size and size-distribution of the distributed nanosized inorganic materials are determined and controlled by the dendritic polymer.

It is yet another object of the present invention to provide a composite antimicrobial composition of matter having improved effectiveness because the dendrimer host is soluble and able to deliver the immobilized metal by its own diffusion, while the metal remains active because of its extremely high surface area It is still a further object of the present invention to provide an improved method of treating wounds, particularly burn wounds.

The foregoing and other objects and advantages of the present invention will hereafter become more fully apparent from the following detailed description.

DESCRIPTION OF THE PREFERRED EMBODIMENTS

Figure 1:
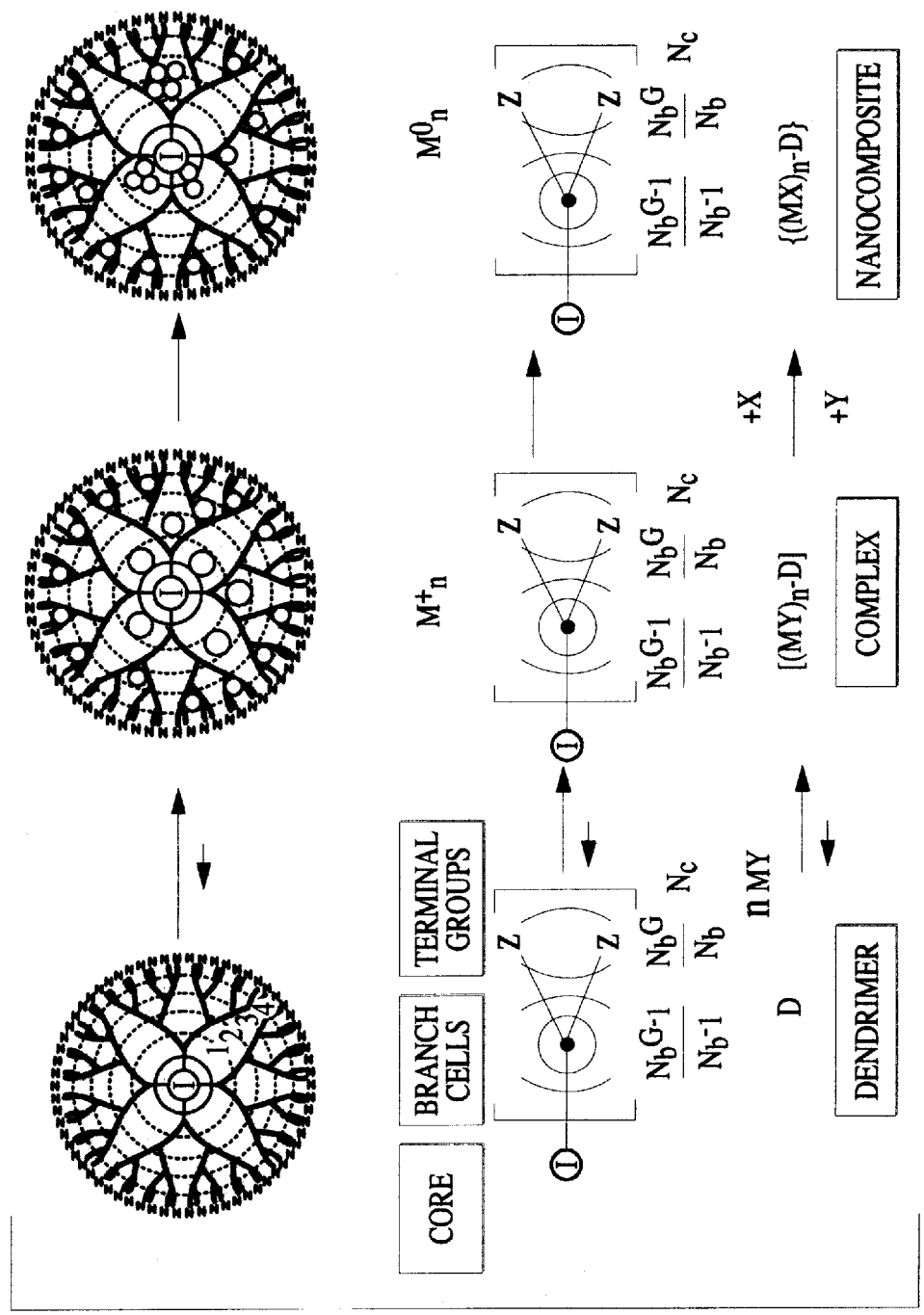
FIG. 1 is a schematic diagram showing the general formation scheme of PAMAM dendrimer complexes and nanocomposites, where $Z=NHC(CH_2OH)_3$ and $Z=OH$, respectively.
Figure 2:
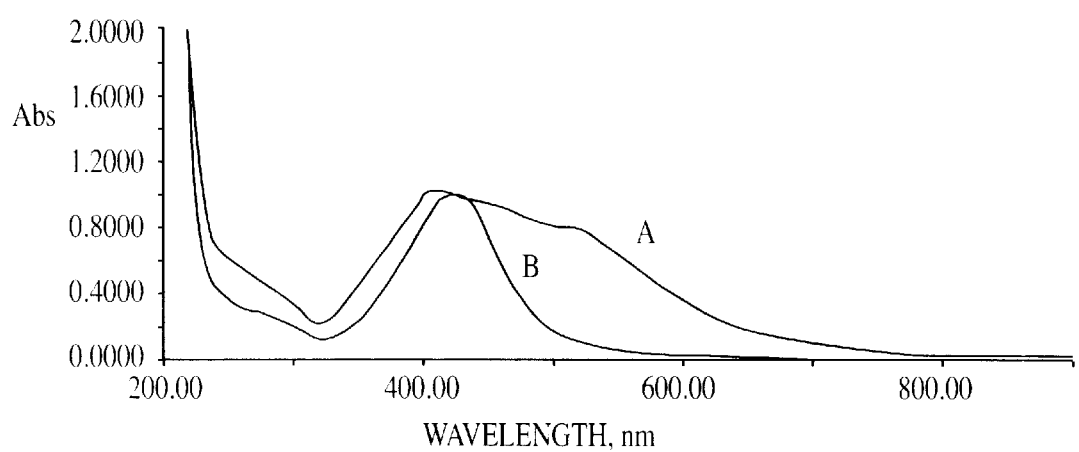
FIG. 2 is a graph showing a comparison of UV-vis spectra of the two nanocomposites, $A=\{(Ag(0))_{256}\text{-PAMAM\_E5.OH}\}$ and $B=\{(Ag(0))_{10}\text{-PAMAM\_E4.T}\}$.

Dendritic polymers, especially dendrimers, can be prepared which have a very narrow size distribution and uniform shape. In particular, dendrimers are symmetrical and spherical macromolecules comprising a relatively dense shell composed of core, branch cells, surface cells, and many terminal groups, which can be identical or different as desired, and an interior that may be similar or very different from the surface of the molecule. Chemical and/or physical properties, such as reactivity, complex or salt formation, hydrophilicity, etc., can be varied and optimized. Dendrimers have been recognized as mono-dispersed nanoreactors, possessing architectures and ligand sites that allow the pre-organization of metal ions on their surface and/or in their interior. Unique physical and chemical properties have been observed in dendrimer based nanocomposites as a consequence of the atomic/molecular level dispersion of the guest in a dendrimer host.

Due to the spherical and monomodal character, diffusion of dendrimers through membranes and cell walls can be controlled as a function of the generation of the dendrimer, and appropriately selected membranes may retain dendrimer hosts with complete (100%) selectivity. Polyamidoamine (PAMAM) dendrimers are stable and soluble in water. A large number of polar terminal groups are concentrated in a relatively thin shell. Accessible tertiary nitrogens in the interior of the dendrimer can form complexes with ions of transition metals, including silver, cerium and zinc. PAMAMs are able to solubilize many organic materials that are commonly considered insoluble in water through guest-host interactions. Bioactive materials including metals, metal ions and organic molecules therefore may be combined in variable concentrations and compositions in one nanoscopic delivery vehicle when dendritic polymers, such as PAMAM dendrimers, are used. Studies using antibody/dendrimer conjugates in vitro and vivo in experimental animals have documented that these conjugates are non-toxic and able to target biologic agents to specific cells.

PAMAM dendrimers with polar surface groups (carboxylate-, amino-, hydroxyl, etc.) are soluble in polar solvents such as water, alcohol, dimethylsulfoxide, etc. The surface of a dendritic polymer can be modified to make the dendrimer soluble in apolar solvents or miscible with apolar carriers. The interior has a polycationic character and forms extremely strong complexes with most of the transition metals. PAMAMs can form salts and complexes with silver, as well as other inorganic ions ($Cs^+$, $Zn^{2+}$, etc.) that have been tested as potential candidates for treating burn wounds. Metal ions can be combined on or within dendrimers, and their concentrations and applied ratios may be varied as desired. PAMAMs also behave as a buffer system because or the tertiary nitrogens in the interior.

Dendrimer-metal nanoscopic size complexes, such as PAMAM-silver composites are believed to have increased antimicrobial activity because they provide a very high local concentration of nanoscopic size silver that is accessible for microorganisms. This silver, in the form of Ag(0), or any other compound, such as AgCl, is bound to the surface and concentrated on the dendrimer with a specific surface area of several thousand square meters per gram. On the other hand, silver compounds reduced into Ag(0) in the absence of dendrimers, form micro-size crystallites with relatively small surface and little adherence to surfaces. Due to the very small size of the nanocomposites (e.g., 20–120 Å), the silver compounds are insensitive to light and photolyse very slowly. Reduction of silver-dendrimers results in nanometer sized particles that adhere strongly to metals, glass and fibers. Silver-dendrimer complexes diffuse together as if they were simply macromolecules. Because of the equilibrium nature of the complex, the dendrimer host gradually releases part of the previously immobilized silver into the environment.

The dendritic polymer-metal nanoscopic size complexes (e.g., dendritic polymer-silver, dendritic polymer-cerium, and dendritic polymer-zinc) are non-toxic, stable and water-soluble. The dendritic polymer-metal nanoscopic sized antimicrobial agents of this invention can be applied as a spray directly to a burn wound after injury. Such application can be applied as first aid without any expertise or the removal of the victim's clothes. Also, PAMAMs can be used to store and solubilize additional biologically active molecules. High functionality dendrimers have a strong absorption on fibers and this property may be utilized, whereby the dress of the injured person could be silver coated after the injury. Also, sterilization of filters is possible.

The antimicrobial agents of this invention are composite compositions of matter in which discrete nanosized inorganic materials (e.g., elemental silver, cerium, zinc, etc.) are distributed on or in a polymeric material (e.g., a dendritic polymer), and in which the size and size-distribution of the distributed nanosized inorganic materials are determined and controlled by the dendritic polymer. The dendritic polymer-metal nanosized antimicrobial agents of this invention are prepared by conjugating a dendritic polymer and a metal known to exhibit antimicrobial activity, such as silver, cerium or zinc.

The dendritic polymers used to prepare the antimicrobial agents of this invention have a preferred mean diameter range of from about 10 to about 1,000 Å. A more preferred mean range is from about 20 to about 150 Å. Generally, any of a variety of dendritic polymers may be used to form the antimicrobial agents of this invention. The individual dendritic polymer nanoreactors can be aggregated together through physical or non-covalent interactions or covalent bonding to form larger clusters if desired. Preferred dendritic polymers include PAMAM dense star polymers. Other preferred dendritic polymers include polypropylamine (POPAM) dendrimers and polyester dendrimers. Other dendritic polymers which may be used include generally any of the known dendritic architectures including dendrimers, regular dendrons, controlled hyperbranched polymers, dendrigrafts, and random hyperbranched polymers. Dendritic polymers are polymers with densely branched structures having a large number of reactive groups. A dendritic polymer includes several layers or generations of repeating units which all contain one or more branch points. Dendritic polymers, including dendrimers and hyperbranched polymers, are prepared by condensation reactions of monomeric units having at least two reactive groups. The dendrimers which can be used include those comprised of a plurality of dendrons that emanate from a common core which can be a single atom or a group of atoms. Each dendron generally consists of terminal surface groups, interior branched junctures having branching functionalities greater than or equal to two, and divalent connectors that covalently connect neighboring branching junctures.

Dendrons and dendrimers can be prepared by convergent or divergent synthesis using methods well known in the art. Divergent synthesis of dendrons and dendrimers involves a molecular growth process which occurs through a consecutive series of geometrically possessive step-wise additions of branches upon branches in a radially outward molecular direction to produce an ordered arrangement of layered branched cells. Each dendritic macromolecule includes a core cell, one or more layers of internal cells, and an outer layer of surface cells, wherein each of the cells includes a single branched juncture. The cells can be the same or different in chemical structure and branching functionality. The surface branched cells may contain either chemically reactive or passive functional groups. Chemically reactive surface groups can be used for further extension of dendritic growth or for modification of dendritic molecular surfaces. The chemically passive groups may be used to physically modify dendritic surfaces, such as to adjust the ratio of hydrophobic to hydrophilic terminals, and/or to improve the solubility of the dendritic polymer for a particular solvent.

Convergent synthesis of dendrimers and dendrons involves a growth process which begins from what will become the surface of the dendron or dendrimer and progresses radially in a molecular direction toward a focal point or core. The dendritic polymer may be ideal or non-ideal, i.e., imperfect or defective. Imperfections are normally a consequence of either incomplete chemical reaction or unavoidable competing side reactions. In practice, real dendritic polymers are generally not ideal, i.e., contain certain amounts of structural imperfections.

Hyperbranched polymers which may be used represent a class of dendritic polymers which contain high levels of non-ideal irregular branching as compared with the more nearly perfect regular structure of dendrons and dendrimers. Specifically, hyperbranched polymers contain a relatively high number of irregular branching areas in which not every repeat unit contains a branch juncture. The preparation and characterization of dendrimers, dendrons, random hyperbranched polymers, controlled hyperbranched polymers and dendrigrafts is well known. Examples of dendrimers and dendrons, and methods of synthesizing the same are set forth in U.S. Pat. Nos. 4,507,466; 4,558,120; 4,568,737; 4,587,329; 4,631,337; 4,694,064; 4,713,975; 4,737,550; 4,871,779 and 4,857,599, incorporated by reference herein. Examples of hyperbranched polymers and methods of preparing the same are set forth, for example, in U.S. Pat. No. 5,418,301, also incorporated by reference herein.

Dendritic polymers suitable for use with the invention also include macromolecules commonly referred to as cascade molecules, arborols, absorbent grafted molecules, and the like. Suitable dendritic polymers include bridged dendritic polymers, i.e., dendritic macromolecules linked together either through surface functional groups or through a linking molecule connecting surface functional groups together, and dendritic polymer aggregates held together by physical forces. Also included are spherical-shaped dendritic polymers and rod-shaped dendritic polymers grown from a polymeric core. The dendritic polymers used in the practice of this invention can be generationally monodispersed or generationally polydispersed. Dendritic polymers in a monodispersed solution are substantially all the same generation, and hence of uniform size and shape. The dendritic polymers in the polydispersed solution comprise a distribution of different generation polymers. The dendritic polymer molecules which may be used in the practice of this invention include mixtures of different interior and exterior compositions or functionalities. Examples of suitable dendritic polymers include polyether dendrons, dendrimers and hyperbranched polymers, polyester dendrons, dendrimers and hyperbranched polymers, polythioether dendrons, dendrimers and hyperbranched polymers, and polyarylalkylane ether dendritic polymers. Polyamidoamine (PAMAM) dendrimers have been found to be particularly useful for preparing the dendritic polymer-metal nanoscopic size antimicrobial agents of this invention. Dendritic polymers which are useful in the practice of this invention include those that have symmetrical branched cells (arms of equal length, e.g., PAMAM dendrimers) and those having unsymmetrical branched cells (arms of unequal length, e.g., lysine-branched dendrimers) branched dendrimers, cascade molecules, arborols, and the like.

Other dendritic polymers which may be used in the practice of this invention include hypercomb-branched polymers. These comprise non-crosslinked poly-branched polymers prepared by (1) forming a first set of linear polymer branches by initiating the polymerization of a first set of monomers which are either protected against or non-reactive to branching and grafting, during polymerization, each of the branches having a reactive end unit upon completion of polymerization, the reactive end units being incapable of reacting with each other; (2) grafting the branches to a core or molecule or core polymer having a plurality of reactive cites capable of reacting with the reactive end groups of the branches; (3) either deprotecting or activating a plurality of monomeric units on each of the branches to create reactive cites; (4) separately forming a second set of linear polymer branches by repeating step 1 with a second set of monomers; (5) attaching the second set of branches to the first set of branches by reacting the reactive end groups of the second set of branches with reactive cites of the first set of branches, and then repeating steps 3, 4 and 5 above to add one or more subsequent sets of branches. Such hypercomb-branched polymers are disclosed in European Patent Publication 0473088A2.

Dendritic polymers, especially dendrimers, may contain coordination moieties or bonding cites which are capable of non-covalently bonding with metals and/or metal-containing compounds to complex with and localize such metals, metal-containing compounds or metalloid-containing compounds within the dendritic polymer. For example, PAMAM dendrimers possess both tertiary amines and amide groups which are present according to mathematically driven dendritic rules. In addition to internal complexation, diffusion resistance towards the surface of the dendrimer increases for any guest molecule or compound due to the radially increasing density of the dendrimer interior. This resistance also increases with the number of generations and provides a diffusion barrier which helps keep complexed molecules or atoms inside the dendrimer. Accordingly, a higher generation dendrimer, such as fourth and higher generation dendrimers, are preferred.

The dendritic polymer-metal nanoscopic size antimicrobial agents of this invention are prepared by contacting a dendritic polymer with a metal ion solution. The metal ion solutions which may be contacted with a dendritic polymer to form the metal-complexes of this invention include inorganic salt solutions in which the metal or metal-containing compounds are present as soluble ions. When such inorganic salt solutions are mixed with dendritic polymers, the metal ions or metal-containing ions diffuse to the dendritic polymer and interact with available binding cites and become complexed by the dendritic polymer, or by a solvent contained within the interior of the dendritic polymer. The solvent, such as water, contained within the dendritic polymer can be different from the solvent in which the outer surface of the dendrimers dissolve. Depending on the internal architecture, and the number, quantity and density of the surface functional groups, complexation may take place in the interior only, or both in the interior and on the exterior of the dendritic polymer. The high local concentration of covalently connected coordination binding sites in the dendritic polymers and the diffusion barrier at the surface of the dendritic polymers enable these molecules to immobilize and retain compounds.

Examples of suitable inorganic salt solutions which can be contacted with dendritic polymers to form metal-containing complexes include metal acetates such as silver acetate, zinc acetate and cerium acetate; and metal sulfates, such as silver trifluoromethanesulfonates. Other examples are set forth in the Example section below.

The soluble metal-containing ion solution is contacted with a dendritic polymer to form a metal-dendritic polymer complex. The dendritic polymer is preferably solubilized in or swelled with a solvent prior to combining with the soluble metal-containing ion solution. The metal-dendritic polymer complex may be subsequently contacted with a reagent which reacts with the complex metal compound to form a different metal compound which is substantially insoluble in the absence of the dendritic polymer.

EXAMPLE

Materials. Dendrimers were purchased from Dendritech and were used without further purification. All other reagents were purchased from the Aldrich Chemical Co., and were used as received.

Instrumentation. IR spectra were recorded on a Nicolet 20DBX FT-IR spectrophotometer between $CaF_2$ plates, UV-visible spectra were obtained on a Cary 1E spectrophotometer at room temperature between 200 and 900 nm in a Suprasil 300 quartz cell (L=1 mm). $^1H$ and $^{13}C$ NMR measurements were carried out by a Varian Unity 300 multinuclear spectrometer equipped with a temperature controller. Size Exclusion Chromatography was performed on three TSK gel columns (4000, 3000 and 2000) using a Waters 510 pump with a Wyatt Technology Dawn DSP-F MALLS and Wyatt Technology 903 interferometric refractometer and a Waters 510 pump with a Waters 410 differential refractometer respectively. A Phillips EM301 instrument was applied for transmission electromicroscopy (TEM) using Formvar coated carbon grids. Atomic absorption measurements were done at the Independent Testing Laboratory of the Saginaw Valley University, Mich. Image analysis was performed on a Macintosh computer using the public domain NIH Image program (developed at the U.S. National Institutes of Health and available on the Internet at http://rsb.nih.gov/nih-image).

Sample Preparation. Generation four, EDA core TRIS modified dendrimer PAMAM_E4.NHC($CH_2OH$)$_3$ with aliphatic OH-surface (E4.T), and generation five, EDA core PAMAM dendrimer with carboxylate terminal groups (E5.OH), were used. Silver containing PAMAM complexes were prepared simply by adding aqueous solutions of the dendrimers to the calculated amount of silver acetate powder. Although $CH_3COOAg$ is hardly soluble in water, it quickly dissolves in the PAMAM solutions. This enhancement is due to the combined action of the silver-carboxylate salt formation and/or to the complex formation with the internal nitrogens. This procedure results in slightly yellow dendrimer-complex/salt solutions that very slowly photolyse when exposed to light into dark brown metallic silver containing dendrimer-silver nanocomposite solutions. Final concentrations of the samples were confirmed by atomic absorption spectroscopy.

Antimicrobial testing. The standard agar overlay method was used. The dendrimer-silver compounds were examined for diffusible antimicrobial activity by placing a 10 μl sample of each solution onto a 6 mm filter paper disc and applying the disc to a dilute population of test organisms distributed over an agar growth medium. Two parallel tests were run, and 10 μl of each agent was used per disc. The standard 24 antibiotic disc panel was run each time as a control. Test organisms (*Staphylococcus arurens, Pseudomonas aeruginosa*, and *Escherichia coli*) were also run against a series of dilution of silver nitrate, ranging from 10% to 0.5%.

Both the silver-dendrimer complexes and the nanocomposites provided antimicrobial activity comparable to those of silver nitrate solutions.

Table 1. Effectivity of PAMAM-silver Complexes and Nanocomposites.

Sensitivity data are given as the diameter of the inhibited area measured in mm. A value of 6 mm represents no inhibition of growth beyond the edge of the standard disc 6 mm filter paper.

TABLE 1

| Tested Compound | % Dendrimer | % Ag(0) | S. Aureus | PS. Aerugino | E. coli |
|---|---|---|---|---|---|
| {Ag(0)-E5.OH} | 2.29 | 0.45 | 11.0 | 10.2 | 8.6 |
| {AgCl-E5.OH} | 2.82 | 0.45 | 10.0 | 9.5 | 8.8 |
| [AgAc-E5.OH] | 3.66 | 0.81 | 12.0 | 10.5 | 8.7 |
| [AgNO$_3$-E5.OH] | 1.76 | 0.31 | 10.3 | 9.7 | 9.0 |

TABLE 1-continued

| Tested Compound | % Dendrimer | % Ag(0) | S. Aureus | PS. Aerugino | E. coli |
|---|---|---|---|---|---|
| [AgAc-E4.T] | 3.66 | 0.66 | 10.9 | 10.4 | 9.5 |
| [AgNO$_3$-E4.T] | 1.76 | 0.35 | 11.1 | 10.2 | 9.4 |
| [AgAc-E4.T] | 9.06 | 0.82 | 11.8 | 10.3 | 9.3 |
| [AgAc-E5.OH] | 10.0 | 2.54 | 14.7 | 12.85 | 10.15 |
| E5.ONa | 3.66 | — | 6 | 6 | 6 |
| E4.T | 3.72 | — | 6 | 6 | 6 |
| 10% AgNO$_3$ | — | 6.35 | 12.85 | 11.05 | 9.8 |
| 7.5% AgNO$_3$ | — | 4.76 | 12.7 | 11.1 | 9.65 |
| 5% AgNO$_3$ | — | 3.17 | 12.65 | 11.2 | 9.5 |
| 2.5% AgNO$_3$ | — | 1.58 | 12.55 | 11.2 | 9.7 |
| 1% AgNO$_3$ | — | 0.635 | 12.3 | 11.1 | 9.8 |
| 0.5% AgNO$_3$ | — | 0.317 | 12.05 | 10.7 | 9.9 |

Interestingly, increased antimicrobial activity was observed with the dendrimer carboxylate salts. We attribute this effect to the a very high local concentration (256 carboxylate groups around a 54 Å diameter sphere[26]) of nanoscopic size silver that is accessible for microorganisms. This silver—either in the form of Ag$^+$, Ag(0), or any other compound, such as AgCl—is bound to the surface and concentrated on the dendrimer with a specific surface area of several thousand m$^2$/g.

Due to the very small size of the nanocomposites used (45–54 Å), these silver compounds are insensitive to light and photolyse very slowly. (Silver compounds, reduced into Ag(0) in the absence of dendrimers, quickly formed micronsize crystallites with little adherence to surfaces. Reduction of silver-dendrimer complexes or salts resulted in nanometer sized clusters that adhered strongly to quartz, glass and fibers. In dialysis experiments silver was retained in the dendrimers, therefore guest and host diffuse together as if they were simple macromolecules. In the absence of dendrimers silver ions quickly precipitate in the form of insoluble silver salts when contacted with chloride and sulfate ion containing solutions. When conjugated to a dendrimer, the silver ions will be transformed into stable silver nanocomposites that remain soluble in the media.

Also, PAMAMs can be used to store and solubilize additional biologically active molecules. Higher generation dendrimers have a strong absorption on fibers and this property may be beneficially utilized wherein the dress of the injured person could be silver-coated after the thermal injury in a form of a spray as first-aid without any expertise or the removal of the victim's clothes.

CONCLUSIONS

Polyamidoamine dendrimer based silver complexes and nanocomposites proved to be effective antimicrobial agents in vitro. Due to the atomic/molecular level dispersion of the guest in a dendrimer host, the activity is retained if the microorganism is able to contact the organized silver domains of the nanocontainers. Macroscopically, the silver remained conjugated to the dendrimer in the form of ions, stable metallic silver clusters or silver compounds. Because the dendrimer host is soluble, it is able to deliver the immobilized silver in the agar medium by its own diffusion. The silver clusters remain active because of their extremely high surface area. Reaction with chloride and sulfate ions neither blocks the diffusion of the silver nor the activity against *S. aureus, Ps. Aeruginosa* and *E. coli*. The protected silver particles displayed high antimicrobial activity in several cases without the loss of solubility. However, whenever required diffusion of dendrimers can be totally stopped if common cellulose membranes are used.

While the invention has been described in this specification with some particularity, it will be understood that it is not intended to limit the invention to the particular embodiments provided herein. On the contrary, it is intended to cover all alternatives, modifications, and equivalents as may be included within the spirit and scope of the invention as defined in the appended claims.

What is claimed is:

1. A method of treating a wound comprising:
    applying to said wound an antimicrobial agent which is a composite material comprising a metal or metal-containing compound distributed on or in a dendrimer;
    wherein said wherein said metal or metal in said metal-containing compound is selected from the group consisting of, silver chloride, silver acetate and silver nitrate.

2. The method of claim 1 wherein said composite material is applied to the wound as a spray.

3. The method of claim 1 wherein said composite material is applied to the wound by first applying said composite material to a cloth substrate and subsequently applying said cloth substrate to the wound.

4. The method of claim 1, further comprising first covering said wound with a membrane to facilitate diffusion of said antimicrobial agent to said wound.

5. The method of claim 4, wherein said membrane comprises a cellulose membrane.

6. The method of claim 1 wherein said metal or metal in said metal-containing compound is selected from the group consisting of silver, cerium and zinc.

7. The method of claim 1 wherein said dendrimer is a polyamidoamine dendrimer.

8. The method of claim 7, wherein said polyamidoamine dendrimer is a generation 4 or generation 5 dendrimer.

9. The method of claim 7, wherein said polyamidoamine dendrimer has aliphatic hydroxyl terminal groups.

10. The method of claim 7, wherein said polyamidoamine dendrimer has carboxylate terminal groups.

* * * * *